(12) United States Patent
Wolf, II

(10) Patent No.: US 12,090,322 B2
(45) Date of Patent: Sep. 17, 2024

(54) RANDOMIZED INTERMITTENT STIMULATION PARADIGM AND METHOD OF USE

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 131 days.

(21) Appl. No.: 17/443,172

(22) Filed: Jul. 21, 2021

(65) Prior Publication Data

US 2022/0023633 A1     Jan. 27, 2022

Related U.S. Application Data

(60) Provisional application No. 62/705,891, filed on Jul. 21, 2020.

(51) Int. Cl.
*A61N 1/36*        (2006.01)
*A61N 1/05*        (2006.01)

(52) U.S. Cl.
CPC ....... *A61N 1/36062* (2017.08); *A61N 1/0551* (2013.01); *A61N 1/36071* (2013.01); *A61N 1/36171* (2013.01); *A61N 1/36175* (2013.01); *A61N 1/36178* (2013.01)

(58) Field of Classification Search
CPC .............. A61N 1/36062; A61N 1/0551; A61N 1/36071; A61N 1/36171; A61N 1/36175; A61N 1/36178
See application file for complete search history.

(56) References Cited

PUBLICATIONS

Sur, Shravani, and Vinod Kumar Sinha. "Event-related potential: An overview." Industrial psychiatry journal 18, No. 1 (2009): 70.
Woodman, Geoffrey F. "A brief introduction to the use of event-related potentials in studies of perception and attention." Attention, Perception, & Psychophysics 72 (2010): 2031-2046.
Coles, Michael GH, and Michael D. Rugg. Event-related brain potentials: An introduction. Oxford University Press, 1995.
Bressler, Steven L. "Event-related potentials of the cerebral cortex." In Electrophysiological Recording Techniques, pp. 103-124. New York, NY: Springer US, 2022.
Patel, Salil H., and Pierre N. Azzam. "Characterization of N200 and P300: selected studies of the event-related potential." International journal of medical sciences 2, No. 4 (2005): 147.
Huang, W. J., W. W. Chen, and X. Zhang. "The neurophysiology of p. 300-an integrated review." Eur Rev Med Pharmacol Sci 19, No. 8 (2015): 1480-1488.

(Continued)

*Primary Examiner* — Paula J Stice
(74) *Attorney, Agent, or Firm* — Schultz & Associates, P.C.

(57) ABSTRACT

The Randomized Intermittent Dichotomous Stimulation (RIDS) paradigm disclosed provides an alternate stimulus for the patient to attend to, besides the typical SCS signal, thus providing a somatotopically-matched non-noxious stimulus to replace the cognitive attention to the nociceptive stimulus. The randomly intermittent stimulus is paired with an implicit virtual task to reinforce selective attention to the non-noxious stimulus.

26 Claims, 10 Drawing Sheets

(56) References Cited

PUBLICATIONS

Kummer, Kai K., Miodrag Mitrić, Theodora Kalpachidou, and Michaela Kress. "The medial prefrontal cortex as a central hub for mental comorbidities associated with chronic pain." International journal of molecular sciences 21, No. 10 (2020): 3440.

Josiassen, Richard C., Charles Shagass, Richard A. Roemer, Stephen Slepner, and Bohdan Czartorysky. "Early cognitive components of somatosensory event-related potentials." International journal of psychophysiology 9, No. 2 (1990): 139-149.

Tarkka, I. M., S. Micheloyannis, and D. S. Stokic. "Generators for human P300 elicited by somatosensory stimuli using multiple dipole source analysis." Neuroscience 75, No. 1 (1996): 275-287.

Huang, Ming-Xiong, Roland R. Lee, Gregory A. Miller, Robert J. Thoma, Faith M. Hanlon, Kim M. Paulson, Kimberly Martin et al. "A parietal-frontal network studied by somatosensory oddball MEG responses, and its cross-modal consistency." Neuroimage 28, No. 1 (2005): 99-114.

Yoshino, Atsuo, Yasumasa Okamoto, Go Okada, Masahiro Takamura, Naho Ichikawa, C. Shibasaki, Satoshi Yokoyama et al. "Changes in resting-state brain networks after cognitive-behavioral therapy for chronic pain." Psychological medicine 48, No. 7 (2018): 1148-1156.

TO FIG. 8B

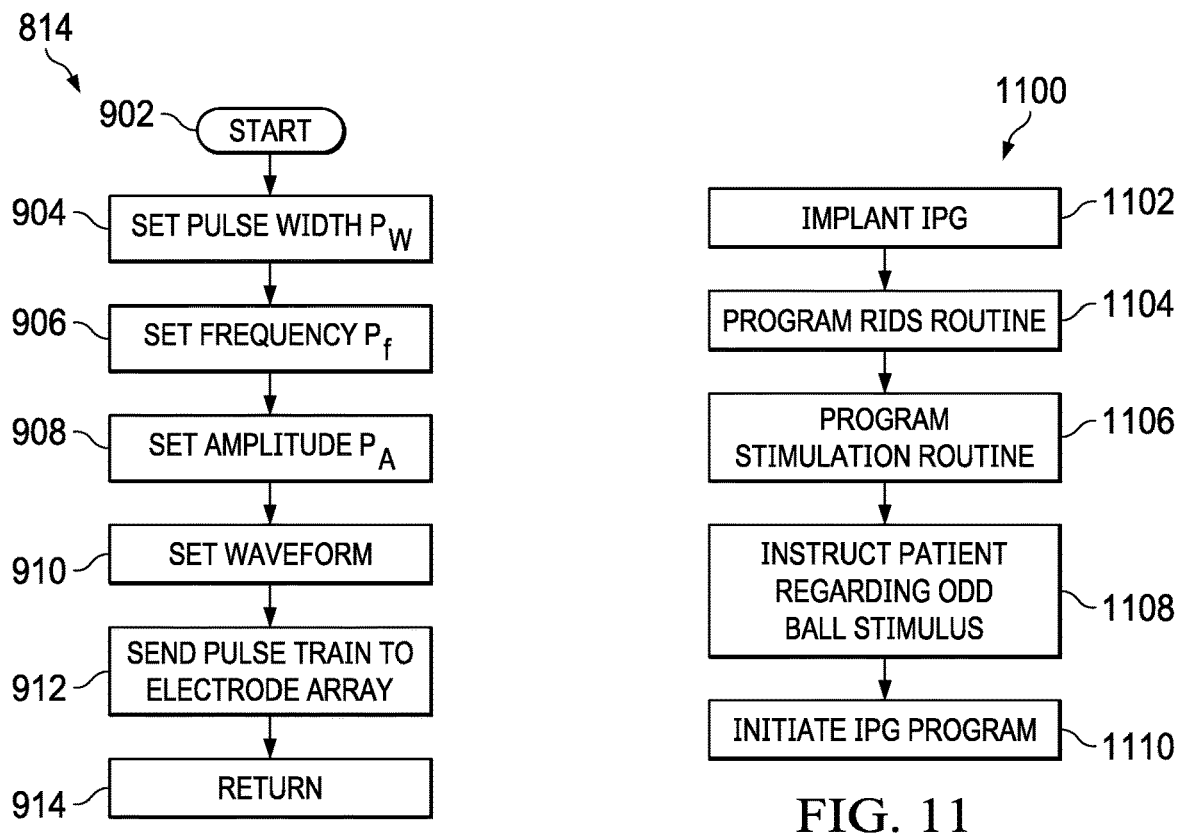
FIG. 9
FIG. 11
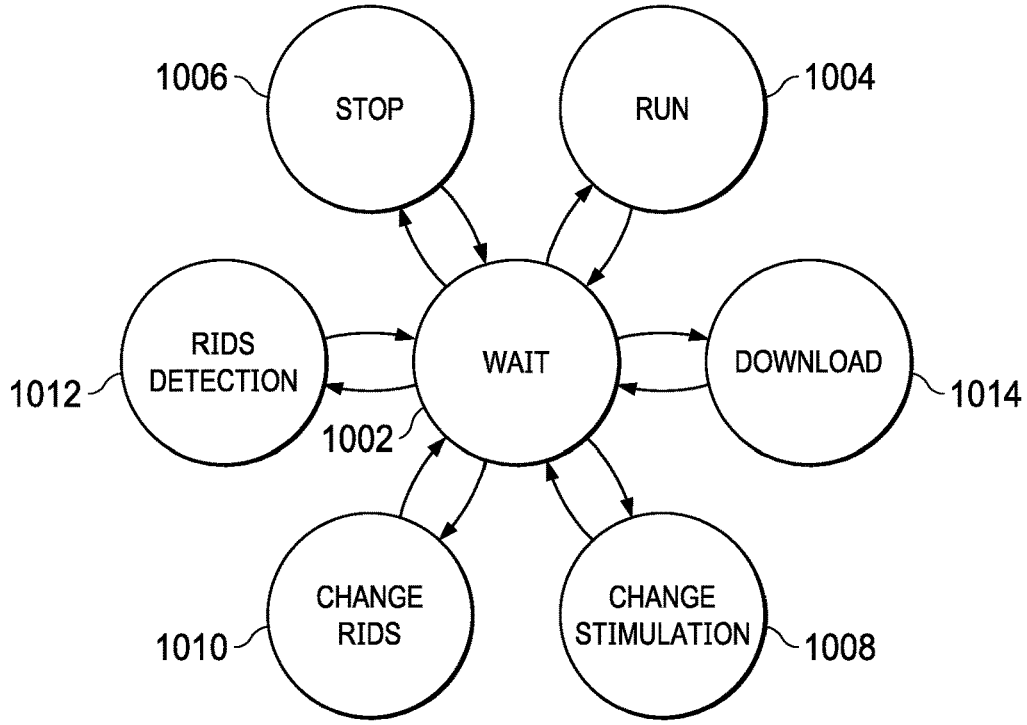
FIG. 10

RANDOMIZED INTERMITTENT STIMULATION PARADIGM AND METHOD OF USE

CROSS-REFERENCE TO RELATED APPLICATIONS

This application claims priority benefits from U.S. Provisional Application No. 62/705,891 filed on Jul. 21, 2020. The patent application identified above is incorporated here by reference in its entirety to provide continuity of disclosure.

FIELD OF THE INVENTION

The field of the invention is randomized intermittent stimulation for enhancing long-term efficacy of spinal cord stimulators.

BACKGROUND OF THE INVENTION

Chronic pain may arise from a variety of conditions, most notably from nerve injury as in the case of neuropathic pain, or from chronic stimulation of mechanical nociceptors such as with spinal pain. Functional ability may be severely impacted by pain, which often is refractory to pharmacological and surgical treatment. In such cases, spinal cord stimulation ("SCS") can be an effective treatment for pain by modulating physiological transmission of pain signals from the periphery to the brain. This may be achieved by applying electrical impulses to the spinal cord via an electrode array implanted adjacent the spinal canal.

SCS has been employed for the treatment of pain since the 1970's. The actual mechanism of action is debated, but a prevailing and durable Gate Control Theory proposed by Ronald Melzack and Patrick Wall in 1965 suggests that pain perception by the brain may be modulated by activation of inhibitory interneurons which downregulate firing of projection neurons within the spinal cord. SCS achieves reduction of pain ostensibly through activation of inhibitory interneurons within these ascending pain pathways. Melzack subsequently concluded that pain is a multidimensional complex with numerous sensory, affective, cognitive, and evaluative components, implicating the role of the brain in overall pain perception.

The cognitive components of pain are well recognized and their importance is clinically evidenced by the partial success of cognitive behavioral therapy ("CBT"). SCS works at the spinal cord level to affect the "gate" but is not known to directly influence the cognitive and evaluative components of pain—potentially limiting the efficacy of conventional SCS, which is well known to diminish over time.

The intermittent nature of nociceptive pain can reinforce the cognitive and evaluative components of pain via selective attention pathways within the brain. Anatomically, the emotional and cognitive components of pain are processed within the medial prefrontal cortex ("MPC") which is composed of the anterior cingulate cortex ("ACC"), prelimbic cortex, and infralimbic cortex. Functional magnetic resonance imaging ("fMRI") studies reveal that there is increased activation of the ACC and decreased activity in the limbic cortices in the context of chronic pain. Ascending pain pathways from the spinal cord project to the medial thalamus which relays nociceptive pain information to the insula, ACC, and somatosensory cortices for discriminative processing of pain, e.g., intensity, location, and quality. The MPC, insula, and limbic system are associated with the affective component of pain and pain memory. Efferent pathways from the MPC project to the periaqueductal grey ("PAG") which exerts descending inhibitory influence on spinal pain pathways. This ACC-MPC-PAG descending inhibitory pathway is believed to mediate placebo-induced pain relief.

Chronic pain models suggest increased MPC activity is associated with pain alleviation, suggesting a potential descending inhibitory pathway to complement the modulation of the ascending pain pathway provided by SCS.

It is well recognized within the electrophysiology literature that randomly intermittent stimuli, or "odd-ball" stimuli, embedded within a pattern of visual or auditory of non-unique stimuli to which a subject attends, will elicit certain event-related brain potentials (e.g., N100, P200, P300, etc.) which are dependent upon factors such as the target stimulus probability, intensity, discrimination difficulty, and whether a response task is associated. Magnetoencephalography has demonstrated that somatosensory odd-ball paradigms elicit event-related potentials localized to the inferior parietal lobule/supramarginal gyms, with subsequent activation of the anterior cingulate cortex and dorsolateral prefrontal cortex. This suggests that intermittent randomized perceptible somatosensory stimuli provided by spinal cord stimulation can activate the ACC-MPC-PAG descending pain-inhibitory pathways.

In FIG. 1, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

Spinal cord stimulators often include an implantable pulse generator (IPG) 32 which delivers electrical stimuli to the spinal cord, typically within the thoracic region, through the electrode lead 31 to an electrode array 30. In many cases, a separate controller 33 is in communication with pulse generator 32 and transmits operational instructions to it. The IPG is typically contained in a titanium canister which is implanted subcutaneously near the upper buttocks or flank and draws power from a battery. The electrode array is connected to the IPG using subcutaneous leads.

The IPG delivers pulses of electrical current to the electrode array, which travel through the electrodes to targeted neurons within the ascending tracts of the spinal cord. The resulting electric field disrupts the perception of pain. Controlling the amplitude of the stimulating electrical field is paramount to success of spinal cord stimulation. Applying inadequate current will fail to depolarize the targeted neurons, rendering the treatment ineffective. Conversely, application of excess current will depolarize the targeted neurons, but also stimulate additional cell populations which renders the perception of a noxious stimulation.

In FIG. 2, representative vertebra 10, a thoracic vertebra, is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal. Surrounding spinal cord 20 is dura 21 that contains cerebrospinal fluid (CSF) 22. Epidural space 24 is the space within the spinal canal lying outside the dura.

Electrode array 30 is typically positioned in epidural space 24 between dura 21 and the walls of spinal canal 16 towards the dorsal aspect of the spinal canal nearest bilateral laminae 15 and spinous process 17.

FIG. 4 shows a detail of electrode array 30 including electrode contacts 35 sealed into elastomeric housing 36. Each electrode contact has a separate electrical conductor in electrode leads 31 so that the current to each contact may be independently controlled. Independent control allows the stimulation signal to be varied top to bottom and left to right, along the array.

SUMMARY OF THE INVENTION

The inventor has recognized that chronic intermittent nociceptive pain is analogous to the odd-ball paradigm used to elicit somatosensory event-related potentials, but with the additional activation of the insular and limbic systems mediating the affective pain component and pain memory. Anticipation of a painful stimulus can induce a prolonged event-related potential known as the contingent negative variation ("CNV"), suggesting this to be a correlate of the cognitive component of pain memory.

The inventor has further recognized that the spinal cord stimulation paradigm may be tailored to activate the ACC-MPC-PAG descending pain-inhibitory pathway without eliciting activation of the affective and memory components of the somatosensory pathways. In traditional modulation of the ascending pain pathways within the spinal cord via SCS, a continuous pattern of electrical stimuli are applied to the dorsal aspect of the spinal cord. Depending upon the paradigm, this may or may not be perceptible to the patient. The stimulating electric field is generally applied to the region of the spinal cord which somatotopically corresponds to the painful area.

The inventor has recognized further that by introducing perceptible intermittent randomized dichotomous (or multi-chotomous) stimuli within the train of otherwise non-unique traditional SCS stimuli and tasking the patient to selectively attend to those unique stimuli, event-related potentials such as the P300 are elicited upon recognition of the unique stimuli. This produces activation of the dorsolateral prefrontal cortex and ACC with efferents to the periaqueductal grey while avoiding activation of the prelimbic and infralimbic cortex. Event-related potential amplitude may be augmented by associating a virtual or physical task with the perception of the target stimulus. Aside from modulating the descending pain-inhibitory pathways, non-noxious somatotopically matched target stimuli may lead to habituation of pain memory, analogous to the tactile attention-shift training and peak end rule memory work components of cognitive behavioral therapy.

The Randomized Intermittent Dichotomous Stimulation ("RIDS") paradigm disclosed provides an alternate stimulus for the patient to attend to, besides the typical SCS signal, thus providing a somatotopically-matched non-noxious stimulus to replace the cognitive attention to the nociceptive stimulus. The randomly intermittent stimulus is paired with an implicit virtual task to reinforce selective attention to the non-noxious stimulus.

By combining conventional SCS with a RIDS paradigm, spinal cord stimulation can downregulate pain via both ascending and descending spinal pathways, as well as modulate the cognitive evaluation of pain, thus improving SCS efficacy and longevity.

The RIDS paradigm consists of a background spinal cord stimulation paradigm and an odd-ball "target" stimulus. The background program may be any paradigm which modulates the electrophysiological function of the spinal cord to downregulate the perception of pain. Suitable background paradigms include tonic stimuli, burst stimuli, high-frequency stimuli, alternating dichotomous stimuli, etc. The background stimuli may be any sequence of stimuli for which there is modulation of inhibitory interneurons at the spinal cord, and, for which there is no significant temporal novelty. The target stimulus is then a perceptibly novel stimulus for which the probability and target-to-target interstimulus interval may be randomized. The target stimulus is preferably somatotopically matched to the painful region. A real or implicit virtual task may be assigned in response to the target stimulus to potentiate the cognitive response to the selective attention.

The incidence of the target stimuli should not be so sparse as to lose selective attention nor so frequent that they become non-novel relative to the patient's pain exacerbations.

BRIEF DESCRIPTION OF THE DRAWINGS

In the detailed description of the preferred embodiments presented below, reference is made to the accompanying drawings.

FIG. 9 is a flow chart of a preferred embodiment of a control program for operation of the transcutaneous control system.

FIG. 10 is a preferred state chart for operation of the transcutaneous control system.

FIG. 11 is a preferred method of use of a preferred embodiment of an IPG implementing a preferred RIDS paradigm.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness.

Figures 1, 4A:
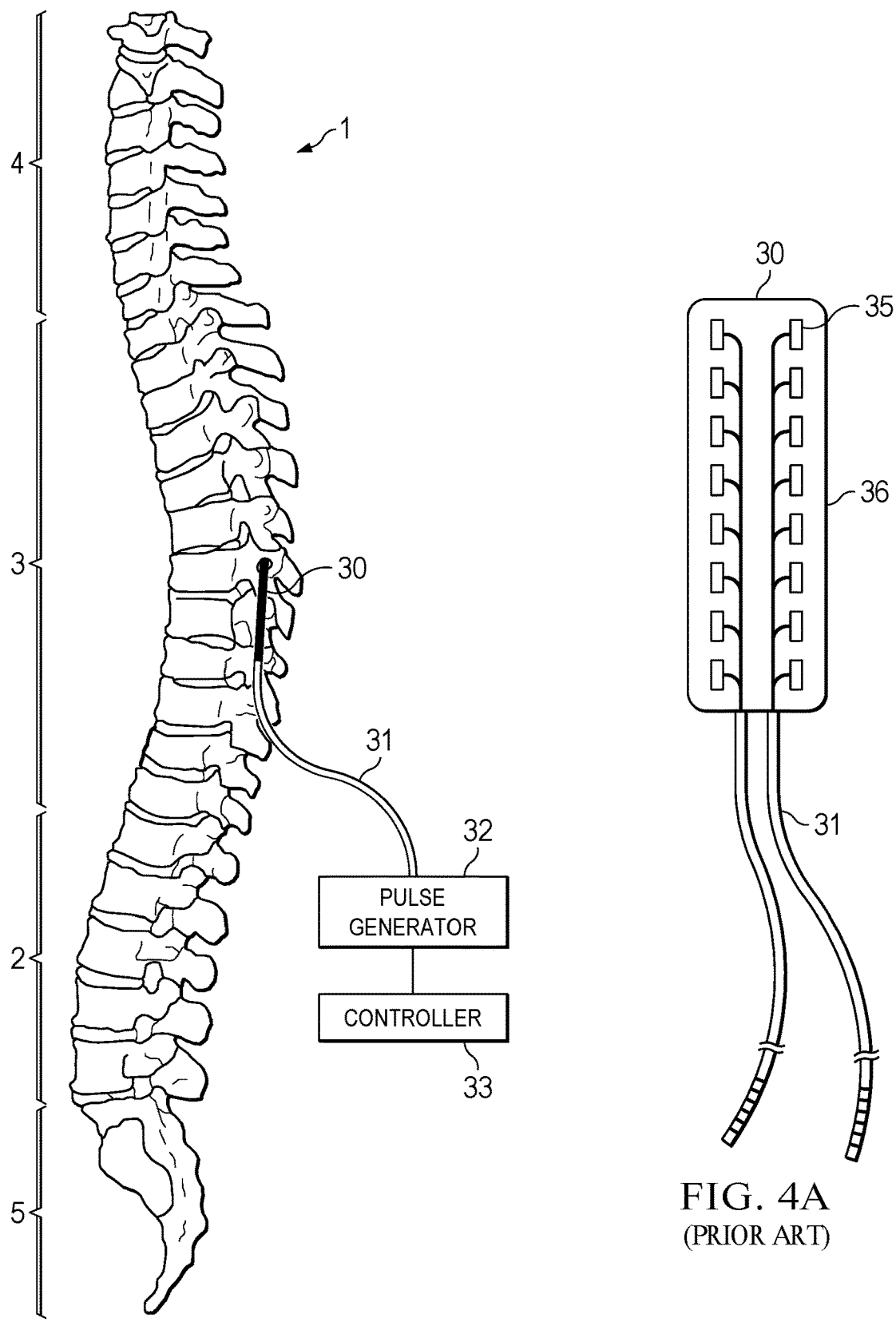
FIG. 1 is a side view of the human spine showing the approximate position of an electrode array for spinal cord stimulation of the prior art.
FIG. 4A shows a prior art surgical electrode array and lead connector for spinal cord stimulation of the prior art.
Figure 2:
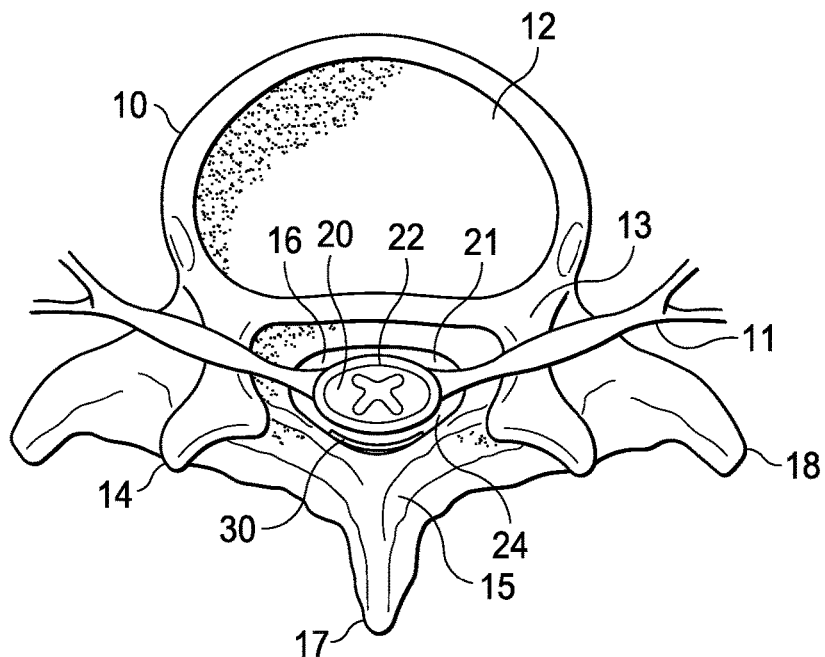
FIG. 2 shows an axial view of a thoracic vertebra indicating the position of the spinal cord and an electrode array for spinal cord stimulation of the prior art.
Figure 3:
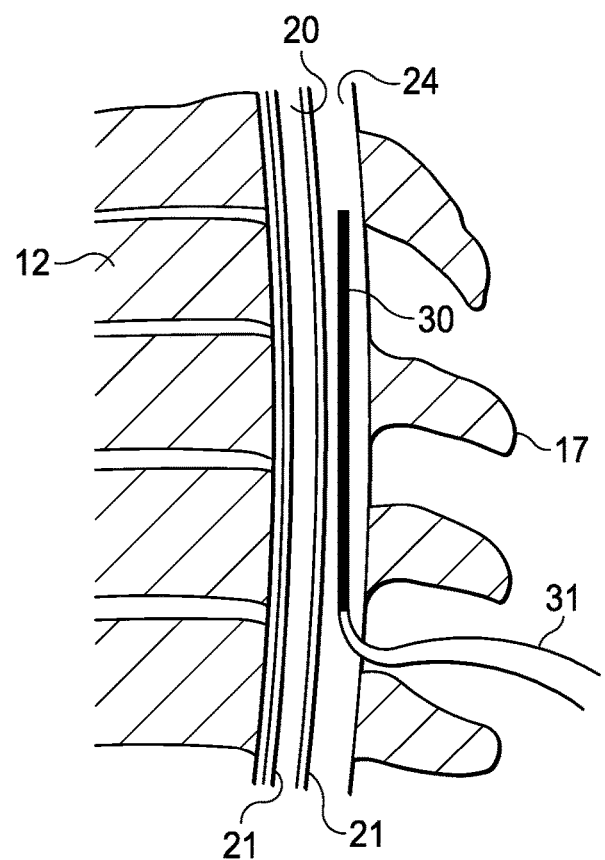
FIG. 3 shows a sagittal cross-sectional view of the human spine showing the approximate position of an electrode array for spinal cord stimulation of the prior art.
Figure 4B:
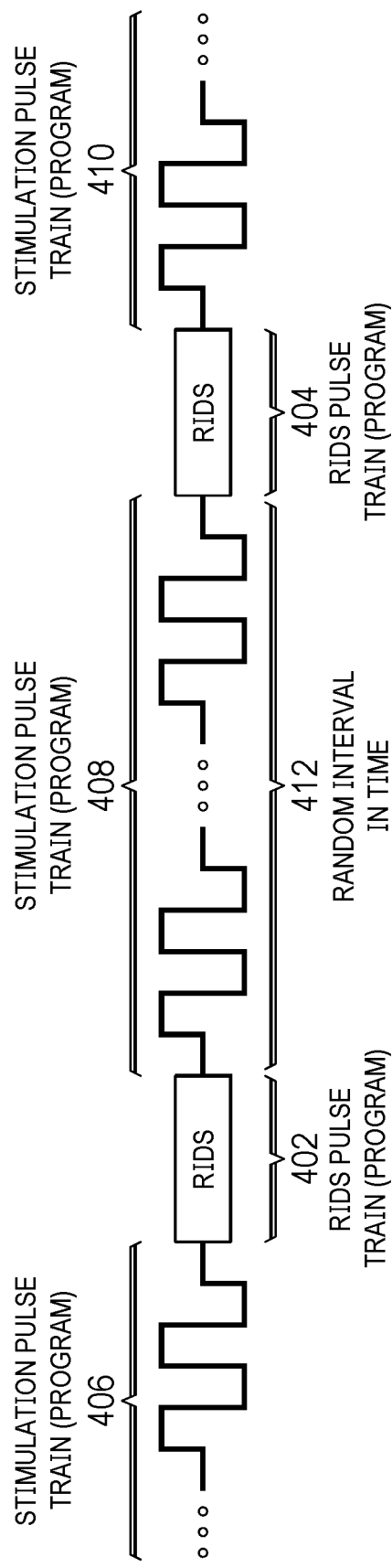
FIG. 4B shows a preferred stimulation pulse train and the RIDS pulse train.
Figure 5:
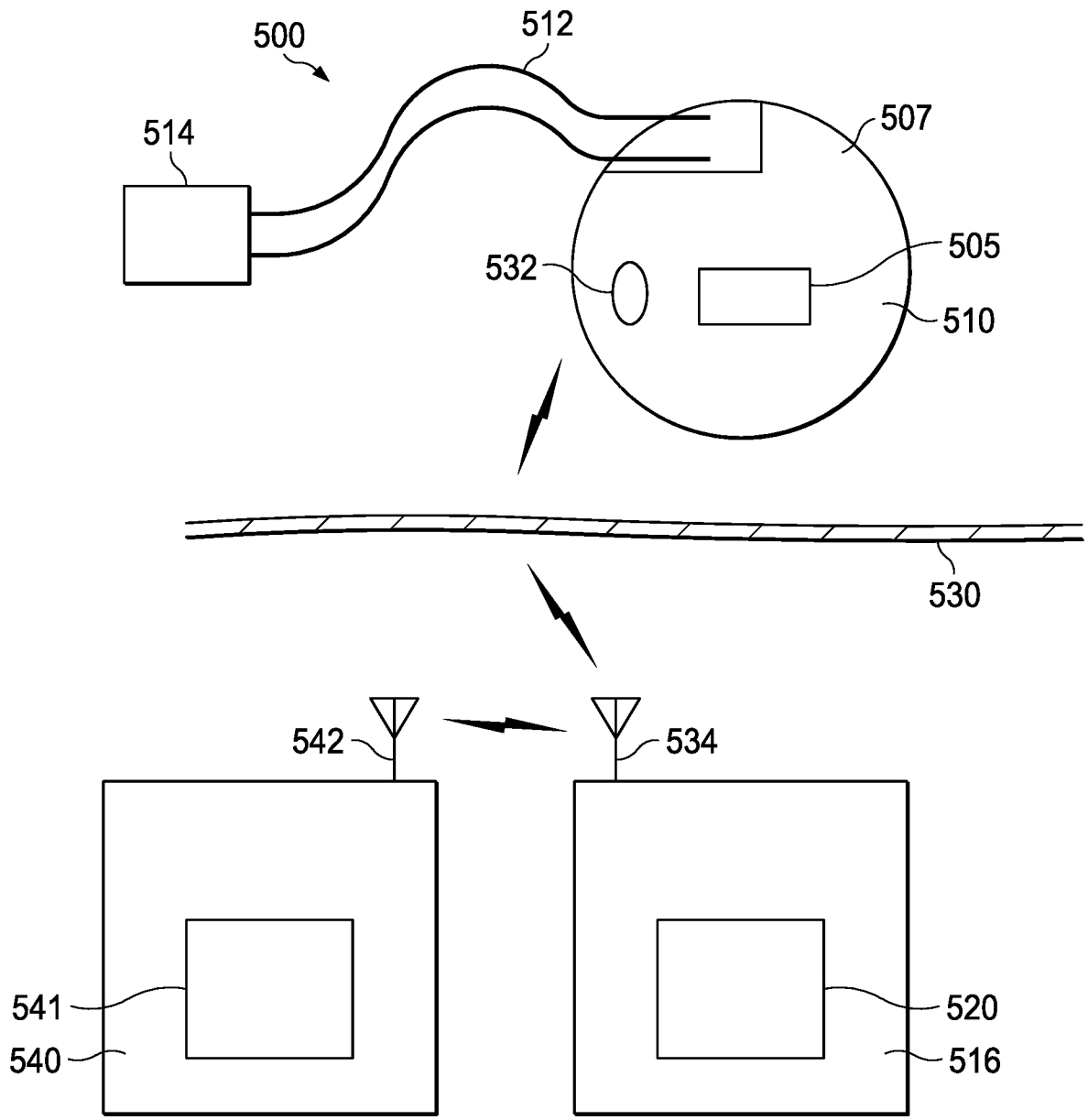
FIG. 5 shows a schematic of an IPG and transcutaneous control system of a preferred embodiment.

Referring then to FIG. 5, preferred IPG system 500 comprises an IPG 510 implanted subcutaneously beneath skin surface 530.

IPG 510 comprises controller 505, operatively connected to RF antenna 532, as will be further described. IPG 510 is preferably battery operated and contained by hermetically sealed case 507, which provides for long term subcutaneous implantation.

In use, controller 505 receives signals from RF antenna 532, for use in communicating data and instructions for operation of the IPG, as will be further described. When active, the controller sends modulated electrical pulses through electrode leads 512 to surgical lead 514, as will be further described.

The IPG system further comprises external system manager 516. External system manager 516 includes controller 520, operatively connected to RF antenna 534.

In use, controller 520 includes a set of instructions which generates a set of operational parameters which are sent to the IPG wirelessly from RF antenna 534 to RF antenna 532, as will be further described.

The IPG system further comprises administrator device 540. Administrator device 540 includes controller 541, operatively connected to RF antenna 542.

In use, controller 541 includes a set of instructions which causes the download of a data table wirelessly from RF antenna 542, containing button press indications received from external system manager 516, as will be further described.

Figure 6:
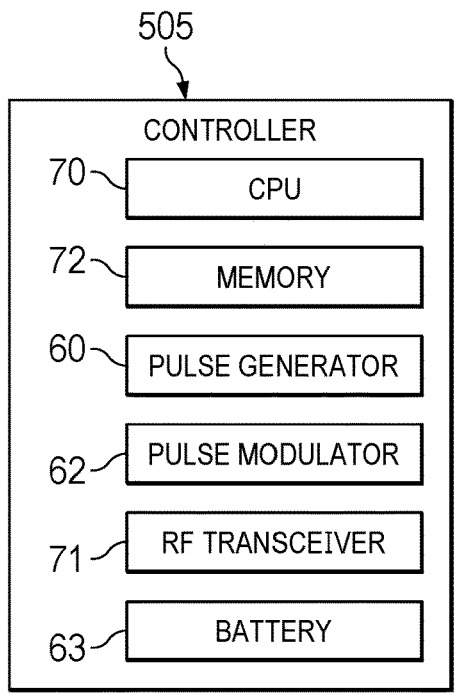
FIG. 6 is an architecture diagram of a preferred embodiment of an IPG.

Referring to FIG. 6, controller 505 will be further described. Controller 505 comprises CPU 70 including onboard memory 72. Controller 505 is further operatively connected to RF transceiver 71, for transmission of status signals and reception of control parameters. CPU 70 is further connected to pulse modulator 62 and pulse generator 60 for generation and transmission of stimulation signals. All components are operatively connected to battery 63, which provides current to operate controller 505.

In order to generate a stimulation pulse to the electrodes, the CPU consults a parameter table stored in onboard memory 72 to determine pulse width $P_W$, pulse frequency $P_f$, pulse amplitudes, $P_A$, and a pulse waveform for each electrode contact in the lead array. The parameters are transmitted to pulse generator 60 which generates the stimulation waveform signal. The waveform signal is passed to pulse modulator 62. Pulse modulator 62 then provides the requisite current to each of the electrode contacts within the lead array.

The stimulation waveform signal of the preferred embodiment is a modified square wave. A preferred embodiment employs pulse widths which may vary from about 20 to 1000 microseconds±10% at a frequency of between about 20 and 1200 hertz±10%. The output amplitude is preferably from about 0 (zero) to ±20 mA or 0 (zero) to ±10 V, but may vary according to patient sensitivity. Other waveform types, pulse widths, frequencies and amplitudes can also be utilized.

The RIDS paradigm randomly intersperses a rare or so called "odd-ball" stimulus into the stimulation waveform signal. The train of pulses that comprises the stimulation waveform signal is one of several options selected by the user using external system manager 516. A train of RIDS pulses is then randomly interjected in the stimulation signal pulse train with a probability specified by a RIDS percentage. The RIDS percentage is the probability that an equivalent length epoch of the stimulation signal pulse train will be replaced by the RIDS pulse train. The RIDS percentage valid range is preferably 0 to 50%, but can be higher, as will be further described.

Figure 7A:
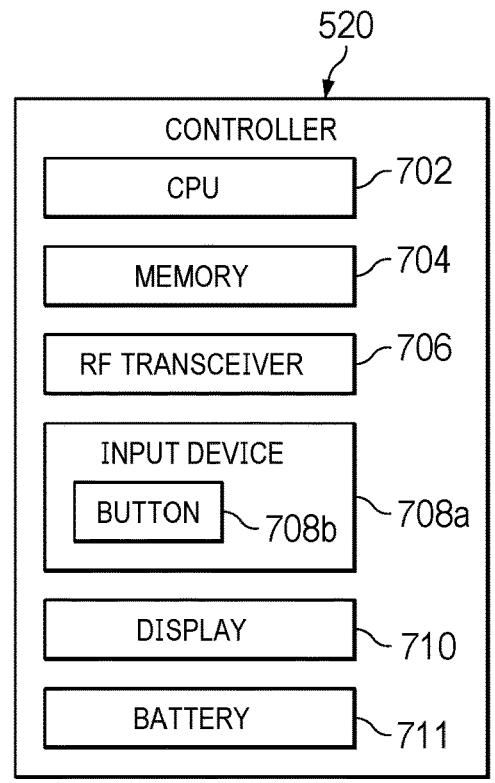
FIG. 7A is an architecture diagram of a preferred embodiment of a transcutaneous control system.

Referring to FIG. 7A, controller 520 will be further described. Controller 520 includes CPU 702 connected to RF transceiver 706, display 710, input device 708, and memory 704. In the preferred embodiment, display 710 is a low power liquid crystal display adapted to show the current operational state of the system. Input device 708 is a simple push button contact array which is constantly monitored by CPU 702. Memory 704 is onboard memory connected to CPU 702. In the preferred embodiment, RF transceiver 706 is a low power transmitter/receiver combination. In the preferred embodiment, all components of the controller draw power from onboard battery 711.

Figure 7B:
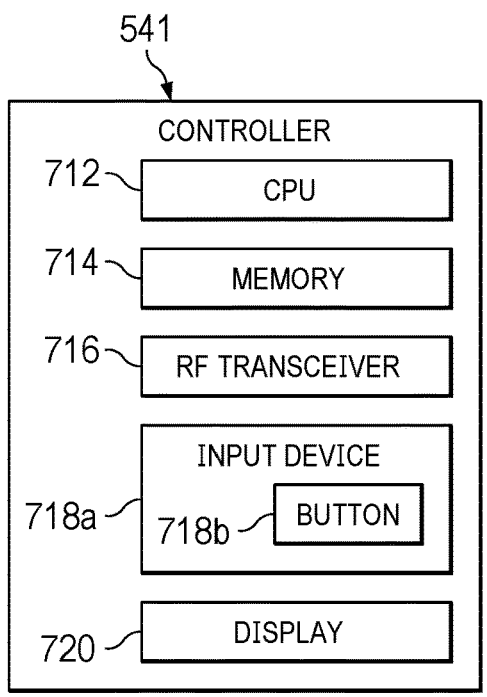
FIG. 7B is an architecture diagram of a preferred embodiment of an administration device.

Referring to FIG. 7B, controller 541 will be further described. Controller 541 includes CPU 712 connected to RF transceiver 716, display 720, input device 718, and memory 714. In the preferred embodiment, display 720 is a low power liquid crystal display adapted to show the current operational state of the system. Input device 718 is a simple push button contact array which is constantly monitored by CPU 712. Memory 714 is onboard memory connected to CPU 712. In the preferred embodiment, RF transceiver 716 is a low power transmitter/receiver combination.

In another preferred embodiment, the components of controller 541 are included in a personal computer, such as a laptop or cell phone which transmits and receives RF signals containing data and instructions via WiFi, infrared or Bluetooth protocols.

Figure 8A:
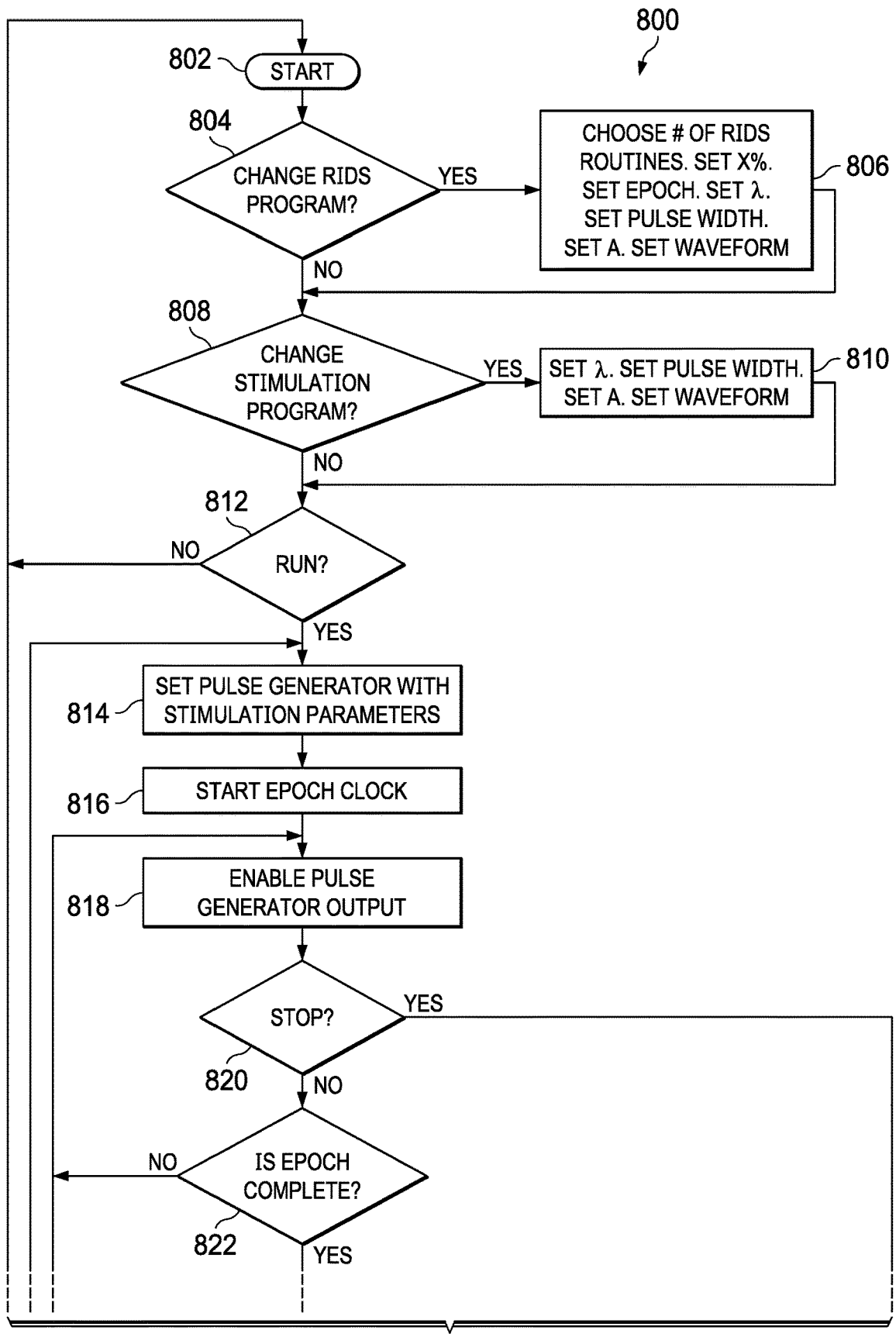
FIGS. 8A and 8B is a flow chart of a preferred embodiment of an IPG program implementing a preferred RIDS paradigm.
Figure 8B:
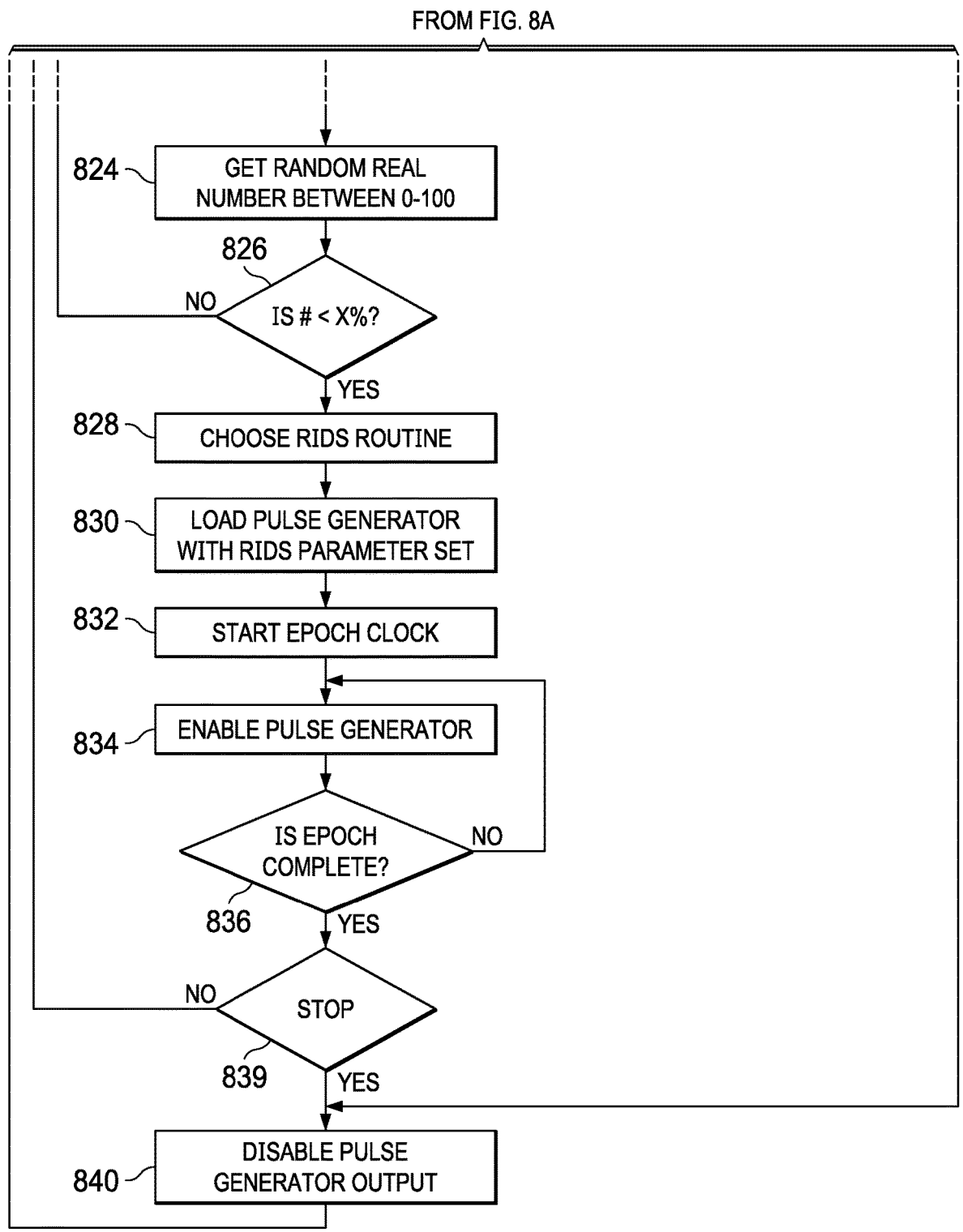

Referring to FIGS. 8A and 8B, method 800 of operation of the preferred IPG will be described.

In a preferred embodiment, method 800 takes the form of a computer program which is resident in memory 72 of controller 505. When activated, the program runs in a continuous cycle.

At step 802, the program begins. RF transceiver 71 is continually polled by the CPU for a "change of operation code" signal to be received from controller 520. In a preferred embodiment, four (4) options are present, "run?", "stop?", "change RIDS program?" and "change stimulation program?".

At step 804, if the operation code "change RIDS program?" is present, the CPU moves to step 806. If not, it moves to step 808.

At step 806, the CPU downloads a number of parameters from RF transceiver 71 and stores them in memory. In a preferred embodiment, the RIDS parameters include a choice of the number of RIDS routines. For each RIDS routine, the CPU further downloads a probability percentage for invoking the RIDS routine during the stimulation program, and an epoch length, a frequency, a pulse width, and an amplitude. The "pulse width" is the duty cycle of the waveform. The probability percentage can be less or much less than 1%. In a preferred embodiment, the probability percentage is between about 0% and about 50%. The CPU then moves to step 808.

At step 808, if operation change code "change stimulation program?" is received, then the CPU moves to step 810. If not, the CPU moves to step 812.

At step 810, the CPU downloads the stimulation pulse parameters including frequency, amplitude, pulse width and, optionally, the waveform from the RF transceiver. Each of the parameters is stored in memory 72. The CPU then moves to step 812.

At step 812, if operation change code "run?" is received, then the CPU moves to step 814. If not, the CPU returns to step 802.

At step 814, the CPU sends a signal to the pulse generator containing the stimulation pulse train parameters, including at least a frequency, a pulse width and an amplitude. In another preferred embodiment, a waveform is also received.

At step 816, the CPU initiates an epoch clock. The epoch clock comprises a counter in time, which accounts for the number of epoch cycles chosen at step 806. In a preferred embodiment, an epoch is the target, or odd-ball, stimulus pulse train duration for the chosen RIDS program.

At step 818, the CPU enables the output of pulse generator 60. Pulse generator 60 effectively generates the stimulation pulse train and then sends it to the pulse modulator which, in turn, adjusts the fractionated current at each electrode contact and sends it to electrode leads 512, for dispersion through lead 514.

At step 820, if operation change code "stop?" is received, then the CPU moves to step 840. If not, the CPU moves to step 822.

At step 822, the CPU polls the epoch clock to determine whether or not it has expired. If not, the CPU returns to step 818. If so, the CPU moves to step 824.

At step 824, the CPU generates a random real number between 0 and 100.

At step 826, the CPU determines whether or not the random real number is less than the RIDS percentage set at step 806. If so, the CPU moves to step 828. If not, the CPU returns to step 818.

At step 828, the CPU elects which RIDS routine to use. In a preferred embodiment, the choice of which RIDS routine to use is made randomly from RIDS routines stored in memory at step 806. In another preferred embodiment, a RIDS routine is chosen from the number of RIDS routines in a predetermined order. However, in another embodiment the choice of which RIDS routine to use is set by user preference based on input from the system manager.

At step 830, the CPU loads the pulse generator with the RIDS parameter set elected at step 828. At step 832, the CPU restarts the epoch clock.

At step 834, the CPU enables the output of pulse generator 60. The pulse generator sends the output to the pulse modulator which disperses it to the leads for activation of the electrodes in the array.

At step 836, the CPU polls the epoch clock to determine whether or not the epoch cycle is complete. If not, the CPU returns to step 834. If so, the CPU moves to step 839.

At step 839, if operation change code "stop?" is present, the CPU moves to step 840. If not, the CPU returns to step 814.

At step 840, the CPU disables the output of pulse generator 60 and returns to step 802.

Figure 8C:
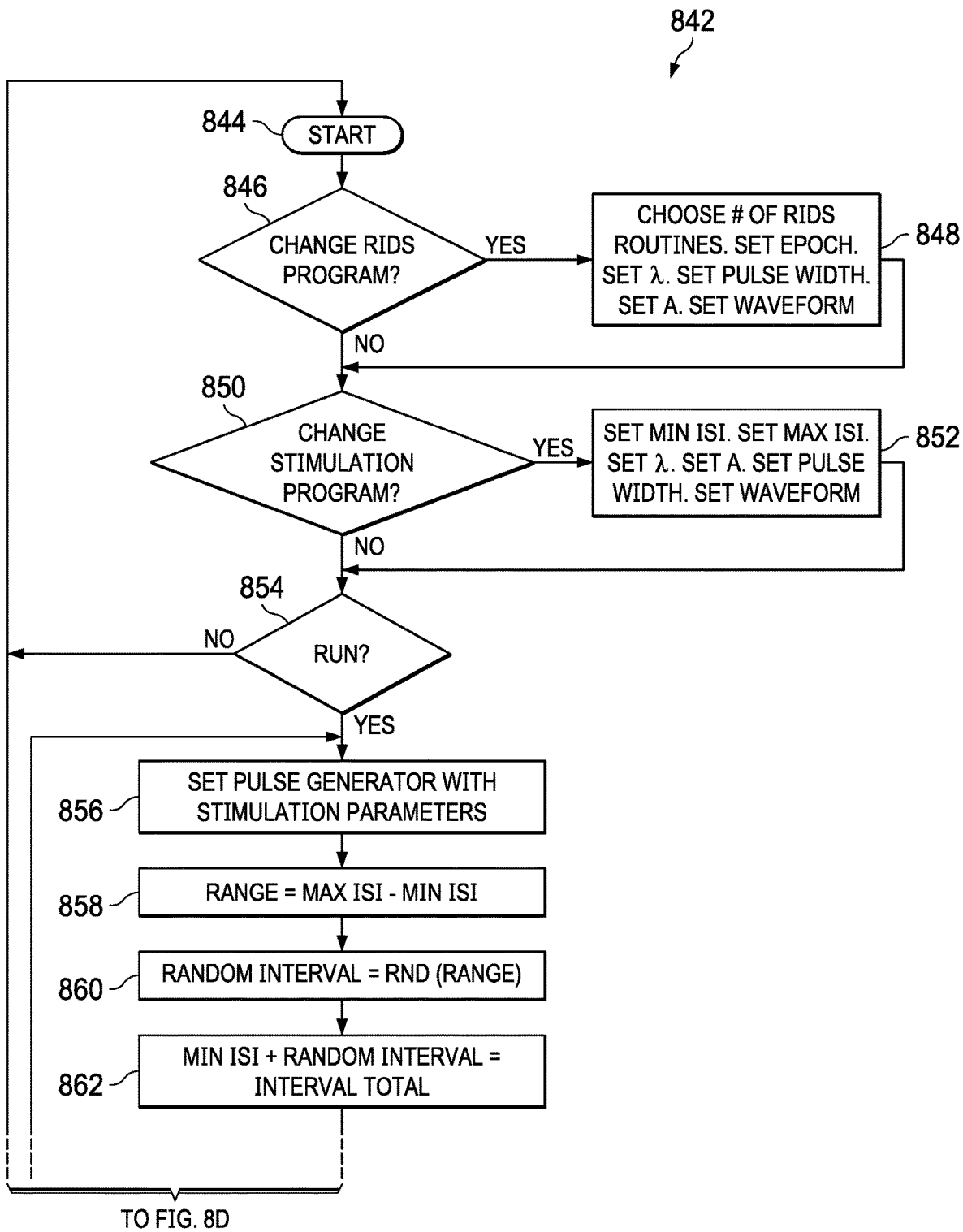
FIGS. 8C and 8D is a flow chart of a preferred embodiment of an IPG program implementing a preferred RIDS paradigm.
Figure 8D:
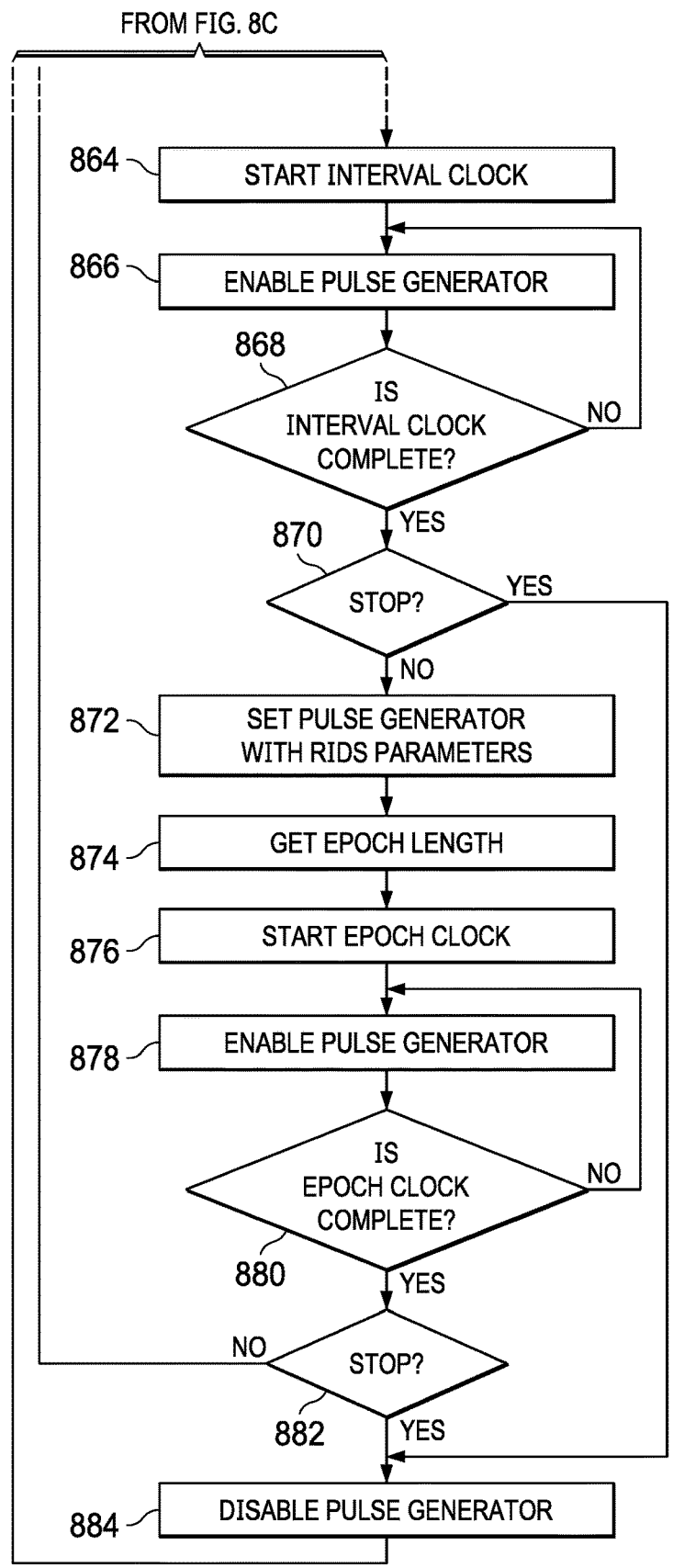

Referring to FIGS. 8C and 8D, an alternate method 842 of operation of the preferred IPG will be described.

In a preferred embodiment, method 842 takes the form of a computer program, which is resident in memory 72 of controller 505. When activated, the program runs in a continuous cycle.

At step 844, the program begins. RF transceiver 71 is continually polled by the CPU for an "change of operation code" signal to receive from controller 520. In a preferred embodiment, four (4) options are present, "run?", "stop?", "change RIDS program?" and "change stimulation program?".

At step 846, if the operation code "change RIDS program?" is present, the CPU moves to step 848. If not, it moves to step 850.

At step 848, the CPU downloads a number of parameters from RF transceiver 71 and stores them in memory. In a preferred embodiment, the RIDS parameters include a choice of the number of RIDS routines available. For each RIDS routine, the CPU further downloads an epoch length, a frequency, a pulse width, an amplitude and optionally a waveform for the RIDS signal. The CPU then moves to step 850.

At step 850, if operation change code "change stimulation program?" is received, then the CPU moves to step 852. If not, the CPU moves to step 854.

At step 852, the CPU downloads a frequency, amplitude, pulse width and optionally a waveform for the stimulation signal. A maximum inter-stimulus interval (MAX ISI) and a minimum inter-stimulus interval (MIN ISI) are also downloaded. The "inter-stimulus interval" is the time between odd-ball pulse trains while the stimulation pulse train is active. In a preferred embodiment, the inter-stimulus interval can range between about 100 seconds and about 12 hours. Other minimum and maximum inter-stimulus interval parameters may be used. Each of the parameters is stored in memory 72. The CPU then moves to step 854.

At step 854, if the operation change code "run?" is received, then the CPU moves to step 856. If not, the CPU returns to step 844.

At step 856, the CPU sends a signal to the pulse generator containing the stimulation pulse train parameters, including at least frequency, pulse width and amplitude. In another preferred embodiment, a waveform is also received.

At step 858, the CPU retrieves the MAX ISI and MIN ISI values from memory and calculates a value for range. "range" is calculated by the following equation.

$$Range = MAX\ ISI - MIN\ ISI$$

At step 860, the CPU picks a random value from the range. In other preferred embodiments, other ranges may be used.

At step 862, the CPU determines an interval total according to the following equation.

$$Interval\ Total = MIN\ ISI + Random\ Interval$$

At step 864, the CPU starts an interval clock. In a preferred embodiment, the interval clock counts from 0 to the interval total, in seconds.

At step 866, the CPU enables the pulse generator to produce the stimulation pulse train, which is sent to the electrodes.

At step 868, the CPU polls the interval clock to determine whether or not it has expired. If not, the CPU returns to step 866. If so, the CPU moves to 870.

At step 870, if the operation change code "stop?" is received, then the CPU advances to step 884. If not, the CPU moves to step 872.

At step 872, the CPU sets the pulse generator with the RIDS stimulation pulse train parameters.

At step 874, the CPU retrieves the epoch from memory.

At step 876, the CPU starts the epoch clock.

At step 878, the CPU enables the pulse generator with the RIDS parameters. The pulse generator generates the RIDS stimulation pulse train which is sent to the electrodes.

At step 880, the CPU polls the epoch clock to determine whether or not it has expired. If not, the CPU returns to step 878. If so, the CPU moves to step 882.

At step 882, if the operation change code "stop?" is received, then the CPU moves to step 884. If not, the CPU returns to step 856.

At step 884, the CPU disables the pulse generator and returns to step 844.

Referring to FIG. 9, the preferred embodiment of step 814, will be further described.

At step 902, the method begins.

At step 904, CPU 70 retrieves a value of signal pulse width, $P_w$, from memory and sends it to the pulse generator.

At step 906, the CPU retrieves a value of signal pulse frequency, $P_f$, from memory and sends it to the pulse generator.

At step 908, the CPU retrieves a value of the signal pulse amplitude, $P_A$, from memory and sends it to the pulse generator.

At step 910 the CPU, optionally, retrieves the signal waveform type from memory and sends it to the pulse generator. Each of these values has been previously received from RF transceiver 71 for the stimulation pulse train and stored in memory, as will be further described.

At step 912, pulse generator 60 and pulse modulator 62 are activated by the CPU to deliver the stimulation pulse train to the electrodes.

At step 914, the method returns.

In a preferred embodiment, the CPU implements the method of FIG. 9, but using the pulse width, pulse frequency, pulse amplitude and optionally a pulse waveform defined for the RIDS pulse train, which are stored separately in memory, to send the RIDS pulse train for step 830.

Referring to FIG. 10, the various states of the controller 520 will be further described.

At state 1002, CPU 702 enters a waiting posture and continually polls input device 708. At state 1004, upon receipt of a "run" signal from the input device, at state 1004, CPU 702 transmits a "run" signal to RF transceiver 706. The RF transceiver then transmits the "run" signal to RF transceiver 71 for further processing. After transmission, CPU 702 returns to wait state 1002.

At state 1006, if a "stop" signal is received from input device 708, CPU 702 passes a "stop" signal to RF transceiver 706 which in turn sends the "stop" signal to RF transceiver 71 for further processing. CPU 702 then returns to wait state 1002.

At state 1010, if a "change RIDS program" signal is received from input device 708, CPU 702 displays an information request on display 710 and then waits for data input from input device 708. CPU 702 then receives a selection of a number of RIDS routines and then a RIDS percentage parameter, a RIDS epoch length parameter, a RIDS pulse amplitude parameter, and a RIDS pulse width parameter, a RIDS pulse frequency parameter and, optionally, a RIDS pulse waveform type parameter, from input device 708, for each individual RIDS routine. These parameters are stored in memory 704 where they are uploaded to RF transceiver 706 for transmission to RF transceiver 71. CPU 702 then transmits a "change RIDS program" signal to RF transceiver 706, which in turn sends the signal and the parameters to RF transceiver 71 for further processing. CPU 702 then returns to wait state 1002.

At state 1008, if a "change stimulation program" signal is received from input device 708, CPU 702 displays a request for input on display 710. CPU 702 then receives a stimulation pulse frequency parameter, stimulation pulse amplitude parameter, a stimulation pulse width parameter and optionally a stimulation pulse waveform parameter from input device 708. The parameters are then stored in memory 704 where they are uploaded to RF transceiver 706 for transmission to RF transceiver 71. CPU 702 then transmits a "change stimulation program" signal to RF transceiver 706, which in turns sends the signal and the parameters to RF transceiver 71 for further processing. CPU 702 then returns to wait state 1002.

At state 1012, if a "RIDS detection" signal is received from input device 708, CPU 702 displays an acknowledgement on display 710. CPU 702 then stores the signal in memory 704, along with its associated timestamp. The RIDS button press and associated timestamp are preferably stored in a running table, indexed by timestamp, for later download to the administrator device 540.

At state 1014, if a "download" signal is received from input device 708, then CPU 702 moves the running table from memory to RF transceiver 706 where it is transmitted to administrator device 540.

In all cases, an appropriate signal is sent to display 710, from CPU 702, to continuously display the operational state of controller 520 and any required information or instructions for the user.

Referring to FIG. 7B, in a preferred embodiment, CPU 712 of the administrator device is programed to continually poll RF transceiver 716, and immediately receives the table and automatically stores it in memory 714, for later retrieval and display based on instructions from input device 718.

Referring then to FIG. 11, a preferred method of use 1100 of a preferred embodiment of an IPG implementing a preferred RIDS paradigm will be further described.

At step 1102, an IPG programmed with a preferred RIDS paradigm is implanted.

At step 1104, the IPG is programmed with an appropriate RIDS routine, as previously described.

At step 1106, the IPG is programmed with an appropriate stimulation routine, as previously described.

Importantly, at step 1108, the patient is instructed regarding the odd-ball stimulation provided by the RIDS routine. The patient is further instructed to imagine undertaking a specific physical task, such as pressing a button, when the RIDS stimulation is perceived or recognized. In another preferred embodiment, the patient is instructed to complete a physical task, such as pressing a button on a key fob, such as input device 708, when the odd-ball stimulus is perceived or recognized.

At step 1110, the IPG program, including the RIDS routine and the stimulation routine is initiated.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

The invention claimed is:

1. A spinal cord stimulator comprising:
   a first processor;
   an electrode adapted to send a stimulation pulse train;
   a pulse generator, operatively connected to the first processor and to the electrode; and
   a first memory, operatively connected to the first processor, containing a first set of instructions that when executed cause the first processor to carry out the steps of:
      delivering the stimulation pulse train, from the pulse generator, to the electrode;
      initiating an epoch clock;
      delivering a first RIDS stimulation pulse train, from the pulse generator, to the electrode, based on the epoch clock; and,
      reinitiating the stimulation pulse train after delivery of the first RIDS stimulation pulse train.

2. The spinal cord stimulator of claim 1, wherein the step of initiating the epoch clock further comprises generating a random number.

3. The spinal cord stimulator of claim 2, wherein the first set of instructions further comprises instructions that when executed cause the first processor to carry out the steps of:
   receiving, at the first processor, a percentage; and
   initiating the first RIDS stimulation pulse train if the percentage is greater than the random number.

4. The spinal cord stimulator of claim 3, wherein the percentage is between 0% and 50%.

5. The spinal cord stimulator of claim 1, wherein the step of initiating the epoch clock further comprises generating a random time interval.

6. The spinal cord stimulator of claim 5, wherein the step of generating the random time interval further comprises the steps of:
   receiving, at the first processor, a minimum inter-stimulus interval and a maximum inter-stimulus interval;
   generating the random time interval between the minimum inter-stimulus interval and the maximum inter-stimulus interval; and
   initiating the first RIDS stimulation pulse train when the random time interval expires.

7. The spinal cord stimulator of claim 1, wherein the first set of instructions further comprises instructions that when executed cause the first processor to carry out the step of:
   disabling the pulse generator when the epoch clock is complete.

8. The spinal cord stimulator of claim 1, wherein the first set of instructions further comprises instructions that when executed causes the first processor to carry out the step of:
   delivering a second RIDS stimulation pulse train, from the pulse generator to the electrode.

9. The spinal cord stimulator of claim 1, wherein the step of delivering the stimulation pulse train further comprises:
   receiving, in the first memory, at least one of a group of, a stimulation pulse train frequency, a stimulation pulse train pulse width, a stimulation pulse train amplitude, a stimulation pulse train waveform, a minimum inter-stimulus interval and a maximum inter-stimulus interval.

10. The spinal cord stimulator of claim 1, further comprising:
    a second processor, in wireless communication with the first processor;
    an input device, operatively connected to the second processor; and
    a second memory, operatively connected to the second processor, containing a second set of instructions that when executed cause the second processor to carry out the steps of:
       receiving a signal, from the input device, indicating a perception of the first RIDS stimulation pulse train by a patient; and
       storing the signal in the second memory.

11. The spinal cord stimulator of claim 10, wherein the second set of instructions further comprises instructions that when executed causes the second processor to carry out the steps of:
    receiving at least one of a group of, a stop signal, a run signal, a change RIDS program signal, and a change stimulation program signal, from the input device; and
    sending at least one of the group of, the stop signal, the run signal, the change RIDS program signal and the change stimulation program signal, to the first processor.

12. The spinal cord stimulator of claim 10, wherein the second set of instructions further comprises instructions that when executed causes the second processor to carry out the step of:
    receiving a RIDS recognition signal from the input device, associated with a patient's recognition of the first RIDS stimulation pulse train.

13. The spinal cord stimulator of claim 12, further comprising:
    a third processor, in communication with the second processor; and
    a third memory, operatively connected to the third processor, containing a third set of instructions that when executed cause the third processor to carry out the step of:
       receiving the RIDS recognition signal from the second processor.

14. A method of spinal cord stimulation comprising the steps of:
    providing an implanted pulse generator, operatively connected to an implanted electrode;
    sending a stimulation signal from the implanted pulse generator to the implanted electrode; and
    substituting a first odd-ball signal for the stimulation signal, at a random time interval.

15. The method of claim 14, further comprising the steps of:
    programming the implanted pulse generator with a stimulation signal parameter set which defines the stimulation signal.

16. The method of claim 15, wherein the step of programming the implanted pulse generator with the stimulation signal parameter set further comprises:
    programing the implanted pulse generator with at least one of a group of, a stimulation pulse train frequency, a stimulation pulse train pulse width, a stimulation pulse train amplitude and a stimulation pulse train waveform.

17. The method of claim 14, further comprising:
    observing a recognition of an odd-ball stimulus perception elicited from a patient upon a patient's perception of the first odd-ball signal.

18. The method of claim 17, further comprises:
    providing a set of instructions to the patient to execute an imaginary task upon the recognition.

19. The method of claim 17, further comprises:
    providing a set of instructions to the patient to execute a physical task upon the recognition.

20. The method of claim 19, further comprising:
providing a processor, operatively connected to the implanted pulse generator;
providing an input device, operatively connected to the processor; and
receiving a signal, from the input device, indicating the recognition of the odd-ball stimulus perception.

21. The method of claim 20, further comprising:
receiving the signal from the input device.

22. A method of spinal cord stimulation comprising the steps of:
providing a processor;
providing an implanted pulse generator, operatively connected to the processor;
providing an implanted electrode, operatively connected to the implanted pulse generator;
sending a stimulation signal pulse train from the implanted pulse generator to the implanted electrode;
calculating, at the processor, a random time interval; and
sending a first odd-ball stimulation signal, from the implanted pulse generator, to the implanted electrode, based on the random time interval.

23. The method of claim 22, further comprising:
programing the implanted pulse generator with at least one of a group of, a minimum inter-stimulation interval time, a maximum inter-stimulation interval time, a stimulation pulse train frequency, a stimulation pulse train pulse width, a stimulation pulse train amplitude and a stimulation pulse train waveform.

24. The method of claim 22, further comprising:
observing a recognition of an odd-ball stimulus perception elicited from a patient upon a patient's perception of a first odd-ball signal.

25. The method of claim 24, further comprises:
providing a set of instructions to the patient to execute a virtual task upon the recognition.

26. The method of claim 24, further comprises:
providing a set of instructions to the patient to execute a physical task upon the recognition.

* * * * *